(12) United States Patent
Sonnenschein et al.

(10) Patent No.: US 8,657,175 B2
(45) Date of Patent: Feb. 25, 2014

(54) MEDICAL DEVICE COMPRISING ALIGNMENT SYSTEMS FOR BRINGING TWO PORTIONS INTO ALIGNMENT

(75) Inventors: Minelu Sonnenschein, Meitar (IL); Yuval Malka, Beer Sheva (IL)

(73) Assignee: Medigus Ltd., Omer (IL)

( * ) Notice: Subject to any disclaimer, the term of this patent is extended or adjusted under 35 U.S.C. 154(b) by 346 days.

(21) Appl. No.: 12/925,273

(22) Filed: Oct. 18, 2010

(65) Prior Publication Data

US 2011/0101068 A1  May 5, 2011

Related U.S. Application Data

(60) Provisional application No. 61/255,892, filed on Oct. 29, 2009.

(51) Int. Cl.
*A61B 17/068* (2006.01)

(52) U.S. Cl.
USPC ........................ 227/176.1; 227/175.1; 227/19

(58) Field of Classification Search
USPC .................................... 227/19, 175.1, 1, 76.1
See application file for complete search history.

(56) References Cited

U.S. PATENT DOCUMENTS

| 7,156,863 | B2 * | 1/2007 | Sonnenschein et al. ...... 606/219 |
| 2001/0056282 | A1 * | 12/2001 | Sonnenschein et al. ...... 606/139 |
| 2011/0295242 | A1 * | 12/2011 | Spivey et al. ................... 606/1 |
| 2012/0199632 | A1 * | 8/2012 | Spivey et al. .............. 227/176.1 |

FOREIGN PATENT DOCUMENTS

| WO | 01/67964 | 9/2001 |
| WO | 02/39909 | 5/2002 |
| WO | 02/068988 | 9/2002 |
| WO | 2005/115255 | 12/2005 |

* cited by examiner

*Primary Examiner* — Brian D Nash
(74) *Attorney, Agent, or Firm* — Roach Brown McCarthy & Gruber, P.C.; Kevin D. McCarthy

(57) ABSTRACT

The invention is a medical device comprising an insertion shaft having an articulation section located near its distal end. The medical device comprises one or more alignment systems to assist in bringing two portions of the insertion shaft that are located on opposite sides of the articulation section into alignment. The alignment systems are selected from the following: a) a mechanical system comprising one or more alignment pins or screws and two or more locking screws located in one of the portions and a corresponding number of funnels and receptacles into which the alignment pins and the locking screws can be inserted or advanced respectively located in the other of the portions; b) an ultrasound system comprising an ultrasound reflecting mirror having one or more steps located on one of the portions and a ultrasound transmitter/receiver located on the other of the portions; and c) an optical system comprising one or more light sources that emit light from one of the portions and an image sensor located on the other of the portions.

14 Claims, 12 Drawing Sheets

(3 of 12 Drawing Sheet(s) Filed in Color)

MEDICAL DEVICE COMPRISING ALIGNMENT SYSTEMS FOR BRINGING TWO PORTIONS INTO ALIGNMENT

REFERENCE TO CO-PENDING APPLICATION

This application claims priority to U.S. provisional patent application Ser. No. 61/255,892; filed on Oct. 29, 2009.

FIELD OF THE INVENTION

The invention is from the field of medical instrumentation. Specifically the invention is from the field of endoscopy. More specifically the invention is methods and devices for aligning two portions of an endoscopic device.

BACKGROUND OF THE INVENTION

In International Patent Applications WO 01/67964 and WO 02/39909 by the applicant of the present application, the descriptions of which are incorporated herein by reference, there are described an articulating endoscope containing a surgical stapler for performing fundoplication procedures for the treatment of gastroesophageal reflux disease (GERD). The stapler consists of two parts, an anvil unit and a staple cartridge unit that are laterally distanced from each other along the axis of the endoscope. In the preferred embodiment of the invention, as disclosed in these applications, the staple cartridge unit is located in a recess in the insertion shaft of the endoscope adjacent to the proximal end of the articulating section, which is located in the esophagus of the patient, and the anvil unit is located in the distal tip of the endoscope at the distal end of the articulating section located in the stomach.

During the endoscopic fundoplication procedure the distal tip is moved relative to the cartridge along a path that is a portion of a circle. As the distal tip approaches the cartridge, layers of tissue of the esophagus and stomach are pressed together. At this stage the staples are fired to connect the layers of tissue together. It is imperative that the final stage of bending of the scope should end such that the distance between the cartridge and anvil and their relative alignment are exactly the distance and alignment required for the legs of the staples to properly curl in the depressions on the face of the anvil. Not achieving proper distance and alignment of the distal tip relative to the cartridge will prevent the tissue from being correctly joined preventing successful completion of the procedure and can potentially pose the risk of serious harm to the patient.

FIG. 1 and FIG. 2 schematically show the distal portion of the insertion shaft of the endoscope described in these PCT applications with the articulation in the straight and fully bent configurations respectively. Shown in these figures are distal tip 10 attached to the distal end of articulation section 14 and the flexible part of the insertion shaft 16 attached to the proximal end of articulation section 14. A staple cartridge unit 18 comprising one or more arrays of staples and a staple firing mechanism are located close to the proximal end of articulation section 14 in a hollowed out portion of a rigid section (not shown in the figures), which connects the insertion shaft 16 to the articulation section 14. A stapler anvil unit 20 is located in distal tip 10.

FIG. 3 schematically shows an illustrative distal tip 10 with anvil unit 20 in place. The five pairs of depressions 22 in which the legs of the staples curl when the staples are fired from the cartridge can be seen on the anvil unit face. Also seen on the face 12 of distal tip 10 are a channel 24 that can be used for example for suction, irrigation, or a working channel, an imaging channel 26, and the distal ends of illumination fibers located in areas 28. The skilled person will understand that other options can be provided and other configurations are allowed depending on the requirements of the endoscopic procedure to be performed. As one example, a transducer, receiver, or reflector can be placed at one of positions 28 for use in ultrasound positioning as described below.

A major technological problem that had to be addressed in the design and in the surgical use of this device is that of achieving and verifying the proper alignment and distance between the two parts of the stapler. Alignment of an object is defined herein as the position and orientation of the object in some coordinate frame, i.e. three translations and three rotations. The term "correct working relationship" is understood herein to mean that the anvil is brought into the exact position opposite the cartridge and that the correct orientation and distance is reached between the face of the anvil and the face of the cartridge that will allow the legs of the staples to enter the depressions provided on the face of the anvil and to be properly curled to hold the layers of tissue being stapled together.

The correct functioning of the endoscopic device depends on the articulation section performing precisely as designed to bring the two parts of the stapler into the correct working relationship as it is bent with a fixed radius R (see FIG. 2). In the early stages of the development of the GERD endoscope it became apparent that it was very difficult and expensive to manufacture a vertebrae section that would consistently perform as required over repeated uses. Even if very precisely designed and manufactured, with time unwanted freedom of motion, or "play" due to "wear and tear" on the individual vertebrae caused by repeatedly bending and straightening the articulation section made the task of attaining the correct working relationship a difficult one.

As said, one of the major technological problems that had to be addressed in the design stage and especially during the surgical application of the endoscopic device was that of achieving and verifying the proper alignment and distance between the two parts of the stapler.

Various solutions to this problem have been suggested and tried by the Applicant. One solution is to provide two locking pins or, preferably, screws that are stored in the anvil portion and can be extended through holes 30 in the face of the anvil (FIG. 3) to engage and lock or be screwed into matching receptacles (not shown in FIG. 3) on the cartridge. When engaged the locking screws not only insure that the correct working relationship between the staple cartridge and anvil has been achieved but also hold the two parts of the stapler together to prevent them from being forced apart during staple firing.

In order to assist in bringing the face of the anvil close enough to the anvil with the proper orientation such that the screws can be extended from the anvil and enter the holes on the cartridge to complete the alignment, an ultrasonic positioning system comprising components on the anvil, cartridge, or both is provided. In International Patent Application WO 02/068988 by the applicant of the present application, the description of which is incorporated herein by reference, there are described ultrasonic techniques that can be used to accomplish the positioning.

Another approach to aiding in achieving the correct working relationship is described in International Patent Application WO 2005/115255 by the applicant of the present application, the description of which is incorporated herein by reference. In this approach, the cartridge and anvil surfaces are given matching curved surfaces. Additionally the curved cartridge surface has a two level structure. As the face of the anvil approaches the surface of the cartridge the tissue to be stapled is pressed between them; and, as a result of the structure of the cartridge surface and the curvatures of both surfaces, the curved surfaces slide over each other pulling the anvil into alignment simultaneously in both the longitudinal and the transverse directions.

It is a purpose of the present invention to provide systems and methods for achieving the correct working relationship of the two parts of a surgical stapler that is an integral part of an articulated endoscope, wherein the anvil of the stapler is located in the distal tip at the distal end of the articulation section of the endoscope and the stapler cartridge is located adjacent the proximal end of the articulation section of the endoscope.

Further purposes and advantages of this invention will appear as the description proceeds.

SUMMARY OF THE INVENTION

The invention is a medical device comprising an insertion shaft having an articulation section located near its distal end. The medical device additionally comprises one or more alignment systems to assist in bringing two portions of the insertion shaft that are located on opposite sides of the articulation section into alignment;

wherein the one or more alignment systems are selected from the group comprising:

a mechanical system comprising one or more alignment pins or screws and two or more locking screws located in one of the portions and a corresponding number of funnels and receptacles into which the alignment pins and the locking screws can be inserted or advanced respectively located in the other of the portions;

an ultrasound system comprising a one or more step ultrasound reflecting mirror located on one of the portions and a ultrasound transmitter/receiver located on the other of the portions; and an optical system comprising one or more light sources that emit light from one of the portions and an image sensor located on the other of the portions.

In embodiments of the invention, the two portions of the insertion shaft comprise a staple cartridge unit located in a hollowed out portion of a rigid section in the insertion shaft of the device adjacent to the proximal end of the articulation section, and an anvil unit located at the distal end of the articulation section in the distal tip of the device.

The medical device of claim 1, wherein the alignment pin/s or screw/s have a diameter of between 1 mm and 3 mm and the opening of the funnel/s has diameter between 2 mm and 6 mm. Embodiments of the invention comprise a mechanism that, when activated, advances the one or more alignment pins or screws out of a first portion of the insertion shaft and continues advancing them until they enter the funnel/s in the second portion of the insertion shaft thereby guiding the two portions into the correct alignment.

Embodiments of the invention comprise a mechanism that, when activated, advances the two or more locking pins or screws out of a first portion of the insertion shaft and continues advancing them until they enter the receptacles in the second portion of the insertion shaft thereby correcting twist of the first portion with respect to the longitudinal axis of the second portion and correcting any residual misalignment.

The ultrasound reflecting mirror in embodiments of the medical device of the invention comprises three steps. The distance between the lower step and the intermediate step of the three step ultrasound reflecting mirror can be either equal to or different from the distance between the intermediate step and the upper step. The areas of the steps is a known percentage of the cross sectional area of the ultrasound reflecting mirror and the known ratio of the areas of the steps can be used to aid in determining the relative alignment of the ultrasound reflecting mirror that is located on one of the portions and the ultrasound transmitter/receiver located on the other portion. In embodiments of ultrasound reflecting the area of the lower step is 50% of the cross sectional area of the ultrasound reflecting mirror and the areas of the intermediate step and the upper step are each 25% of the cross sectional area of the ultrasound reflecting mirror.

In embodiments of the medical device of the invention wherein the ultrasound reflecting mirror comprises three steps, the correct working relationship between the two portions is achieved when an image of the ultrasound beam reflected from the three step ultrasound reflecting mirror that is displayed on the screen of a display device comprises three signals with a predetermined distance between the signals and a predetermined relationship between the intensities of the signals. If the area of the lower step is 50% of the cross sectional area of the ultrasound reflecting mirror and the areas of the intermediate step and the upper step are each 25% of the cross sectional area of the ultrasound reflecting mirror, then the predetermined relationship between the intensities of the signals is that the reflected intensities from two steps are equal and their magnitude is half of the reflected intensity from the third step.

In embodiments of the medical device of the invention the ultrasound and optical alignment systems can be connected to an external system comprising hardware, including a processor, a display screen, and software that is adapted to receive and interpret the received signals from the alignment systems and convert these signals into visual or audible signals to the surgeon instructing him in which direction and how much to bend the articulation section. These embodiments can comprise one or more electric motors controlled by the external system processor and software to bend the articulation section in two mutually perpendicular directions and to activate the alignment screw and the locking screws.

In embodiments of the medical device comprising a stapler, the staple cartridge unit can comprise one or more channels that pass through the staple cartridge unit to allow light emitted from one or more light sources mounted on the insertion tube of the device below the cartridge to exit the face of the cartridge as parallel beams of light in a direction essentially perpendicular to the surface of the cartridge. Mounting the one or more light sources on the insertion tube of the device below the cartridge prevents heating of tissue in contact with the surface of the cartridge. In other embodiments the light sources can be replaced by one or more optical fibers or coherent fiber optic bundles that conduct light having one or more wavelengths through the interior of the endoscope from the proximal end to the entrance/s to the one or more channels in the staple cartridge unit. Alternatively one or more light sources can be mounted on or just below the surface of the staple cartridge.

The image sensor of the medical device of the invention can be an imaging means that is implemented in the device and used for visualization during execution of the medical procedure. In embodiments of the invention the imaging means that is implemented in the device is a video camera comprising either a CCD or a CMOS imaging element.

In embodiments of the medical device of the invention that comprise both an optical and a mechanical alignment system, the optical system may comprise a lens or lens system having a focal length that is longer than the distance at which the alignment pins or screws are inserted into the funnels to focus the light from the light source.

In embodiments of the invention that are connected to an external system the processor can comprise software that is adapted to execute image processing methods to enhance the image recorded by the image sensor in order to compensate for the smearing of the image caused by scattering by tissue between the light source and the imaging sensor and to increase the signal to noise ratio and provide a usable image on the display screen. With these embodiments the distribution of the intensity measured by each pixel in the enhanced image can be used to provide an indication of the position of the image sensor relative to the light source. If two or more light sources are used, the distribution of the intensity measured by each pixel in the enhanced image can be used to provide an indication of the alignment of the image sensor relative to the light source.

Embodiments of the medical device may comprise a filter which passes only selected wavelengths of the light emitted by the light source.

Embodiments of the medical device that are connected to an external system comprising a screen to display the enhanced images of the light sources may also comprise a screen overlay comprising one circle for each light source used. Each circle has a predetermined diameter and location, wherein the diameters of the circles and locations of the centers of the circles are determined such that when the image of the each light source is centered on and fills its respective circle on the screen the two portions of the insertion shaft are in the correct working relationship.

For embodiments of the medical device that comprise an optical alignment system, the distance between the light source and image sensor can be determined directly from measurements of the reflected light intensity using either one light source or using two light sources having different wavelengths.

All the above and other characteristics and advantages of the invention will be further understood through the following illustrative and nonlimitative description of preferred embodiments thereof, with reference to the appended drawings. In the drawings the same numerals are sometimes used to indicate the same elements in different drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

The invention is a medical device comprising an insertion shaft having an articulation section located near its distal end. The medical device additionally comprises one or more alignment systems to assist in bringing two portions of the insertion shaft that are located on opposite sides of the articulation section into alignment.

The one or more alignment systems are selected from the group comprising:
  a mechanical system comprising one or more alignment pins or screws and two or more locking screws located in one of the portions and a corresponding number of funnels and receptacles into which said alignment pins and said locking screws can be inserted or advanced respectively located in the other of the portions;
  an ultrasound system comprising a three step ultrasound reflecting mirror located on one of the portions and a ultrasound transmitter/receiver located on the other of the portions; and
  an optical system comprising one or more light sources that emit light from one of the portions and an image sensor located on the other of the portions.

An illustrative example of the medical device of the invention is the endoscopic stapler and medical procedures described in International Patent Applications WO 01/67964 and WO 02/39909 referenced herein above. Henceforth the invention will be described in terms of the endoscopic stapler. Skilled persons will know how to modify the description mutatis mutandis herein to describe other types of medical devices.

Mechanical Alignment System

Figure 4:
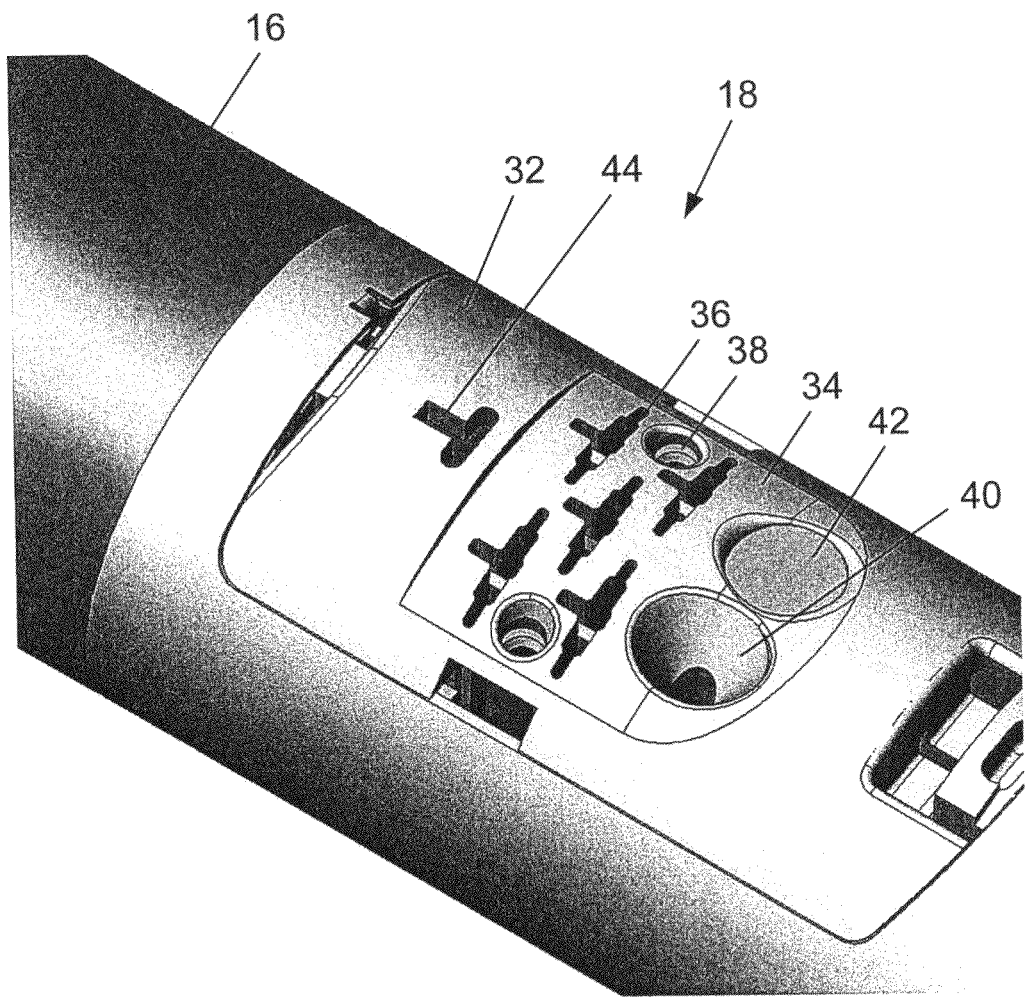
FIG. 4 shows a staple cartridge unit locked in position inside a hollowed out portion of insertion shaft of the endoscopic device.

FIG. 4 shows a staple cartridge unit 18 locked in position inside a hollowed out portion of insertion shaft 16 of the endoscopic device. The convex curved surface of cartridge unit 18 consisting of upper level 32 and lower level 34 is seen in the figure. In the lower level are shown five slots 36 through which the staples are ejected when the firing mechanism is activated, the entrances to two receptacles 38 into which the locking screws in the anvil unit can be advanced, a ultrasound reflecting mirror 42, and a funnel 40 into which an alignment pin or screw located in the anvil unit can be inserted.

In previous embodiments of the endoscopic device, the ultrasound system was used to guide the distal tip close to the correct position opposite the face of the anvil and then the screws were advanced out of the face of the anvil unit towards the receptacles in the cartridge. The entrance of the receptacles is beveled and when each of the screws hits the beveled surface it slides into its respective receptacle and the anvil unit is "pulled" into exact alignment as the screws are turned advancing into the bores. The screws are threaded into the bores until the ultrasound system indicates that the correct distance between the face of the anvil unit and the surface of the cartridge unit is attained. At this point the anvil and cartridge are locked together with the exact orientation and distance that allow safe firing of the staples.

Figure 5:
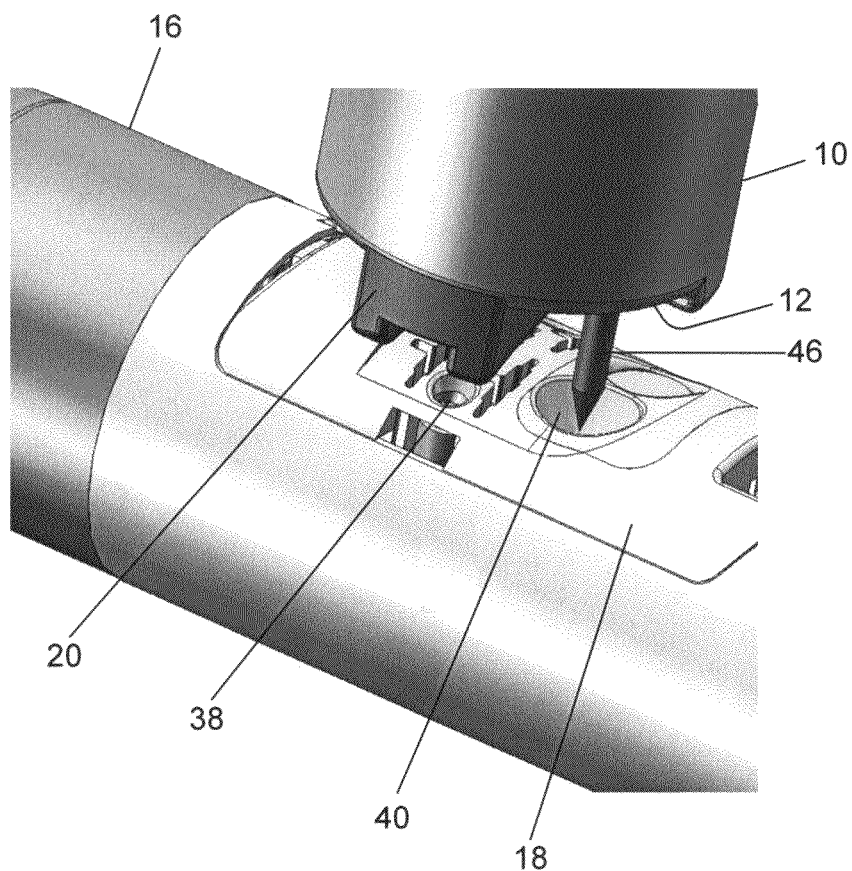
FIG. 5 shows the distal tip and staple cartridge when the articulation section has been bent through nearly its maximum bending angle.

Because of space limitations the funnels at the entrances to bores 38 that are located in the cartridge are approximately 2 mm in diameter; therefore, in practice, attaining the initial alignment that allows both screws to enter the corresponding receptacles is frequently a time consuming and tiring task. The solution to this problem provided by the present invention is to separate the two functions of the screws and to provide a larger diameter funnel as a part of new element to aid in the alignment. FIG. 5 shows the distal tip and staple cartridge when the articulation section has been bent through nearly its maximum bending angle. As the distal tip 10 approaches the staple cartridge 18, a mechanism is activated that advances an alignment pin or screw 46 out of the distal face 12 of distal tip 10. Alignment pin 46 penetrates the layers of tissue that are located between the anvil 20 and the cartridge 18 and enters the funnel 40 that has been created in the stapler cartridge 18. Alignment pin 46 typically has a diameter of between 1 mm and 3 mm, which is the maximum diameter pin that can pierce the tissue without damaging it, and the opening of funnel 40 has diameter of between 2 mm and 6 mm. Mechanical bending of all but the most severely worn articulation section accomplishes the alignment within the degree of accuracy required to allow alignment pin 46 to enter funnel 40. Even when this has been accomplished, the face of the anvil 20 can be twisted with respect to the longitudinal axis of the staple cartridge 18 with the result that if the two locking screws are extended from the face of the cartridge, one or both of them will not enter the receptacles 38. However, after alignment pin 46 enters funnel 40, the articulation section is bent further. The curved face of the anvil pivots about alignment pin 46 and slides over the curved surface of staple cartridge 18 (as described in the above mentioned WO 2005/115255) settling over the lower level 34 of the cartridge surface with exactly the required orientation between the two parts of the stapler. The two screws are then advanced out of the anvil unit and screwed into the receptacles 38 to adjust residual misalignment and the distance and to lock the anvil and the cartridge in the correct working relationship.

Figure 15:
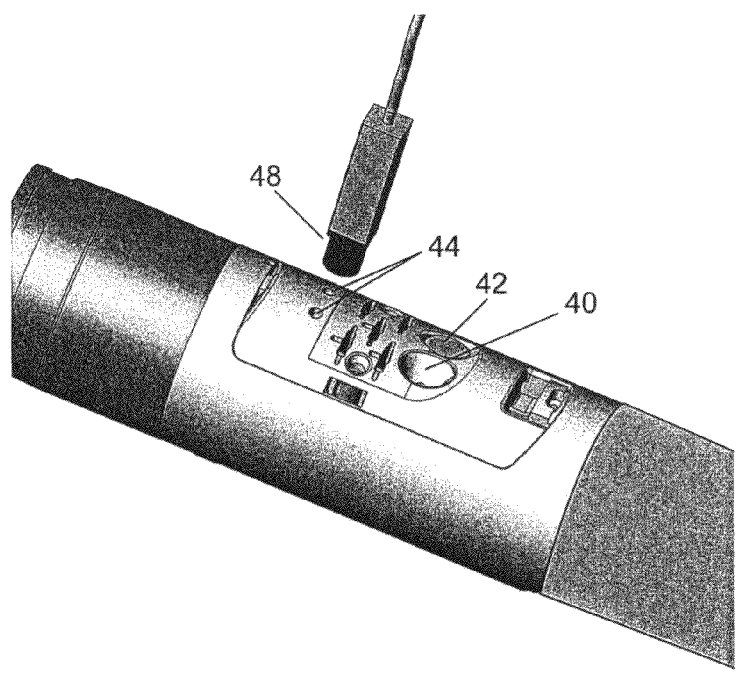
FIG. 15 schematically shows the basic configuration of the optical alignment system of the invention.

Referring to FIG. 4, also shown in upper level 32 is the upper end of a channel 44 that passes through the staple cartridge unit to allow light emitted from a laser diode, vertical cavity surface emitting laser (VCSEL), light emitting diode (LED), or any other type of light source that can be mounted in the hollowed out portion of the rigid section below the cartridge to exit the face of the cartridge as parallel beams of light in a direction essentially perpendicular to the surface of the cartridge for use in the optical alignment system that will be described with reference to FIG. 15 to FIG. 20' herein below. One or more channels can be provided for one or more laser diodes or LEDs. The LEDs can have any of a variety of shapes that can be advantageously employed in the optical alignment system; for example FIG. 4 shows a channel for use with a single "T" shaped LED and FIG. 15 shows the openings in the surface of two channels 44 for use with two circular LEDs.

Alternatively, the laser diodes or LEDs could be mounted directly in the cartridge near the surface. However, since the staple cartridge is replaced after every procedure, this embodiment is more expensive and more difficult to implement because of the electrical connections to the light source.

In an another embodiment, an illumination source can be located outside of the endo scope and an optical fiber or a coherent fiber optic bundle used to conduct the light having one or more wavelengths through the interior of the endoscope from the proximal end to the channel/s 44 in the staple cartridge unit.

Ultrasound Alignment System

Figure 6:
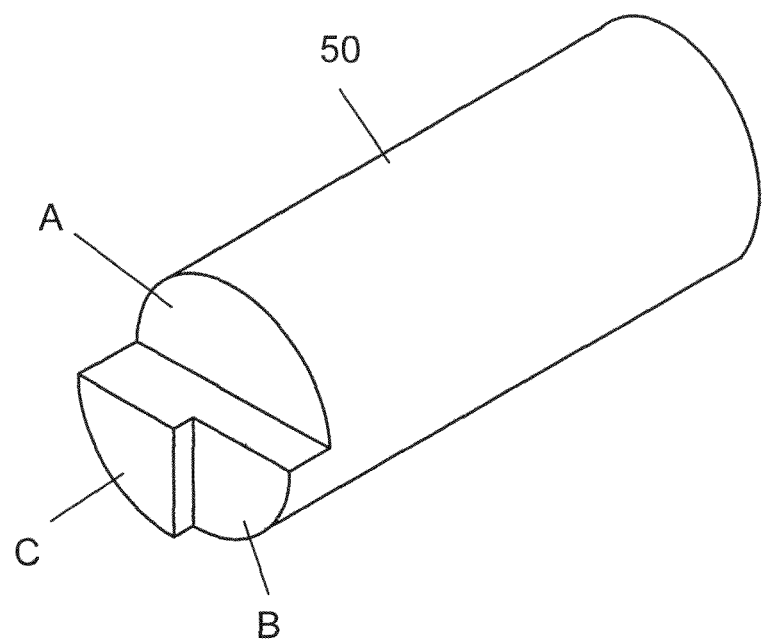
FIG. 6 shows a three step insert 50 that is inserted into the staple cartridge.

FIG. 6 shows an insert 50 that is inserted into the staple cartridge in place of the ultra sound mirror 42 (see FIG. 4). The top of insert 50 is comprised of three steps that each reflects ultrasound energy. The area of the lower step A is 50% of the cross sectional area of the insert and the areas of the intermediate step B and the upper step C are each 25% of the cross sectional area of insert 50. The heights of the steps can be used to suggest the direction of the steering required to bring the two components into alignment as will be described below. For the example discussed with respect to FIGS. 6 to 14 the height of A-B is 70 μm, the height of B-C is 50 μm, and therefore A-C is 120 μm. Insert 50 is oriented so that the planar surfaces of the steps are essentially parallel to the surface of the staple cartridge unit. The planar surfaces of the steps of insert 50 are ultrasound mirrors that will reflect a narrow beam of ultrasound energy emitted by a transducer on the distal face of the endoscopic device back towards the transducer, where the reflected energy will be detected if the ultrasound transmitter/receiver is facing the cartridge surface in the area of insert 50.

In an embodiment of the invention, the three step reflector can be created directly on the top of the staple cartridge unit and a separate insert is not needed.

Figure 7:
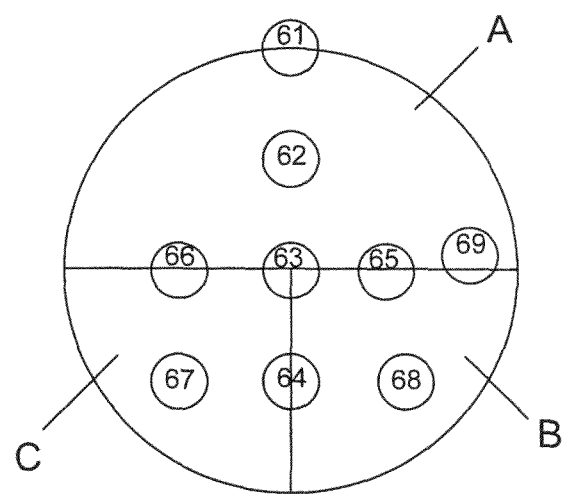
FIG. 7 is a diagram showing the reflecting surfaces of the three step insert with small circles superimposed to designate eight distinct locations where the transmitted ultrasound beam can strike the surface.

FIG. 7 is a diagram showing the reflecting surfaces of the three step insert 50 with small circles 61 to 69 superimposed to designate nine distinct locations where the transmitted ultrasound beam can strike the surface. The return times and intensities of the reflected beam from each of these locations will be different and can be used to determine the exact location of the ultrasound transducer, i.e. the distal tip/anvil unit, relative to the three step insert, i.e. the stapler cartridge unit. Therefore the pattern of the reflected signals can be used to "steer" the distal tip in order to achieve the correct working relationship between the anvil and the cartridge.

FIG. 8 to FIG. 14 are screen shots showing the intensity (vertical axis) vs. distance the beam has traveled (horizontal axis) of the signals of a narrow ultrasound beam reflected from each of locations 61 to 69.

Figure 8:
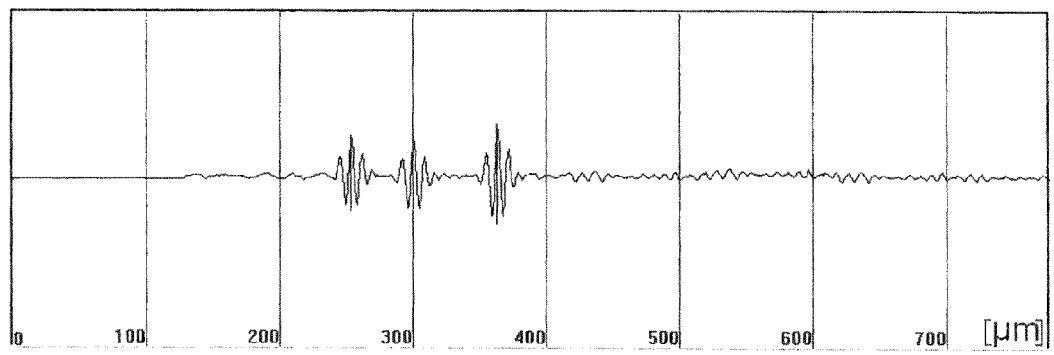
FIG. 8 to FIG. 14 are screen shots showing the signals of a narrow ultrasound beam reflected from each of locations shown in FIG. 7 respectively.

FIG. 8 shows the return signal from a beam that impinges on location 63 at the exact center of three step reflecting surfaces. As can be seen, there are three reflected signals. The first at about 250 μm is for the beam that travels the shortest distance, i.e. the part of the beam reflected from step C. The second signal at about 300 μmm is for the portion of the beam reflected from step B and the third signal at about 370 μm is for the portion of the beam reflected from step A. The difference between the echoes is the height of the steps which is 50 μm, 70 μm and 120 μm respectively. The ratios of the intensities of the reflected signals also confirms their origin since as expected, if the transmitted beam strikes the reflecting surfaces exactly at location 63, then the origin of 50% of the reflected energy should be step A and the source of remaining reflected energy should be equally divided between step B and step C. If the ratio of the intensities of the three signals is not exactly as shown in FIG. 8, then the transducer, i.e. distal tip, should be moved slightly to the left or right or up or down until the exact alignment is achieved.

If no return signal is received then this is an indication that the transmitted beam has missed the insert 50 entirely and the articulation section should be partially straightened and bent again. For an endoscopic device that has been properly maintained this is a rare occurrence since the tolerances of the mechanical bending of the articulation section are sufficiently tight to bring the transducer opposite the insert.

Figure 9:
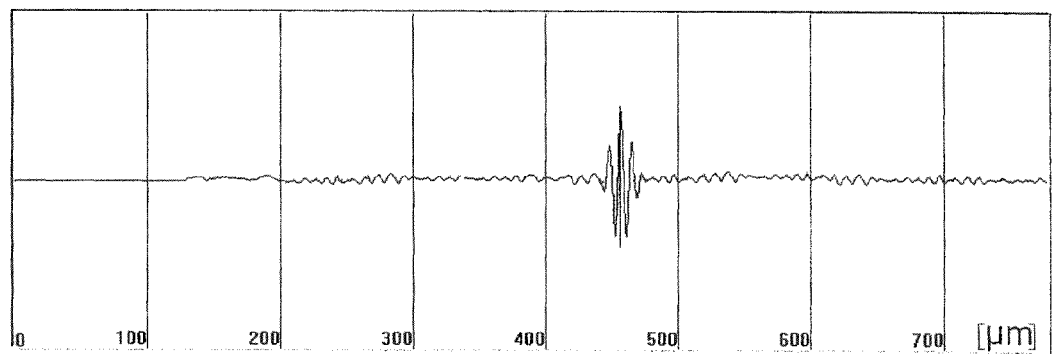
Figure 10:
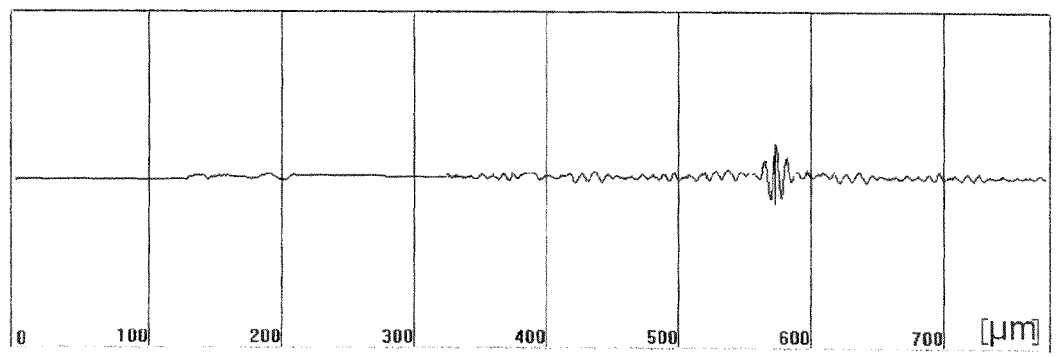
Figure 11:
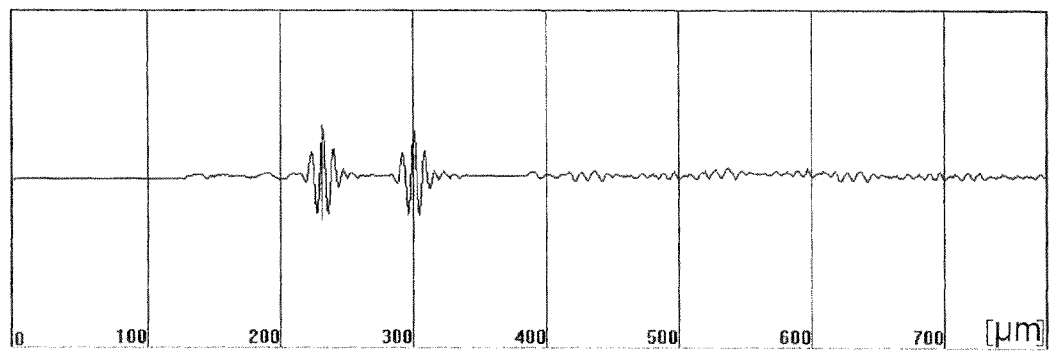

If one strong return signal, such as is seen in FIG. 9, is displayed on the screen then the surgeon knows that the transmitted beam has been reflected from one of the steps but it is not possible to know which one of them, i.e. the beam might have been reflected from any one of locations 62, 67, or 68. If a single weak signal, such as seen in FIG. 10, is displayed on the screen then the surgeon knows that the transmitted beam has been only partially reflected from one of the steps, i.e. the transmitted beam has only partially hit the target, e.g. at location 61. In this case, the distal tip and consequently the beam must be slowly moved until the signal strength has been achieved.

If only one return signal is displayed, then the beam is steered until two signals are received. Two reflected signals indicate that the transmitted beam has struck the insert at the border between two of the steps, e.g. at locations 64, 65, or 66. Further information can be obtained from the distance between the reflected signals. If the distance between two echoes is 50 μm as in FIG. 14, then the beam must be on the border between step B and step C, e.g. at location 64. If the distance is 70 μm as in FIG. 11, then the beam must be on the border between step A and step B, e.g. at location 65. If the distance is 120 μm as in FIG. 13, then the beam must be on the border between step A and step C, e.g. at location 66.

Figure 12:
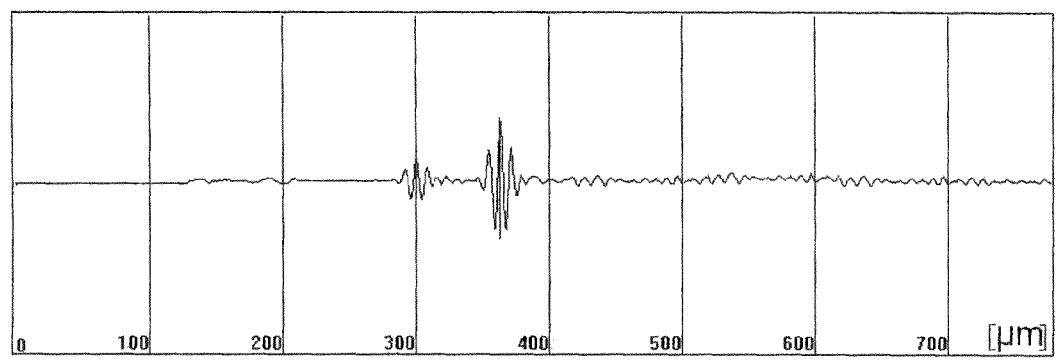
Figure 13:
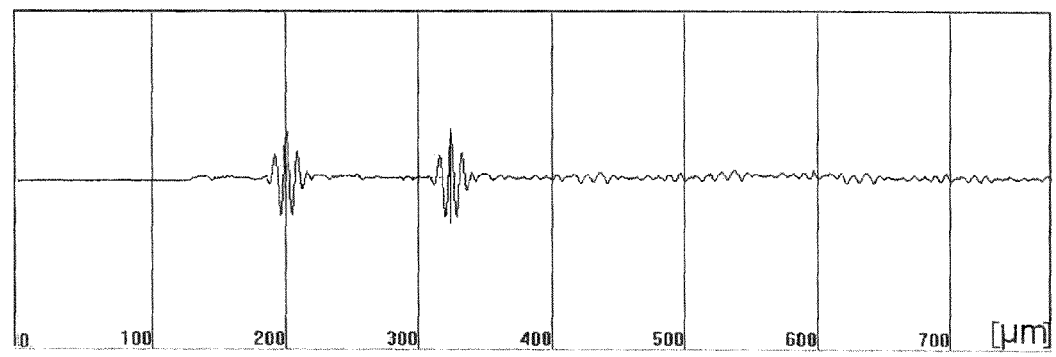
Figure 14:
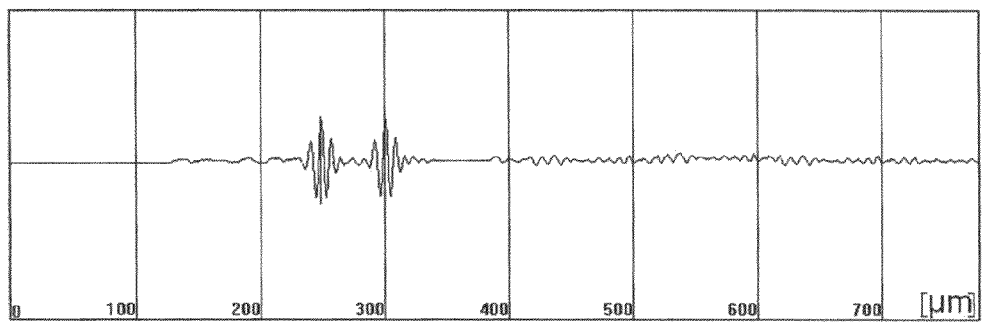

The relative intensities of the two signals are used to position the beam exactly on the border of two adjacent steps. For example a display such as shown in FIG. 12 indicates that the transmitted beam has struck the surface of the insert at the border between two steps that are 70 μm apart with about ⅔ of the beam on one step and ⅓ on the other, e.g. at location 69. The interpretation of FIG. 12 suggests that the beam should be steering down to achieve two signals of equally intensity, then the beam steered right or left staying on the border between two steps until the intersection of the borders of all three steps, i.e. location 63, is found.

The endoscopic device is designed such that the correct working relationship between the anvil and stapler is achieved when the image seen in FIG. 8 is seen on a display screen provided with the endoscopic system. Using the principles discussed above, the surgeon uses the bending mechanism of the articulation section to steer the distal tip up and down and twists the endoscope for steering left and right until the screen shot of FIG. 8 appears indicating that he has achieved the desired alignment. After this he extends the alignment pin and locking screws out of the anvil unit into the cartridge.

In practice, the surgeon does not have to directly observe and interpret the reflected ultrasound signals displayed on the display device. Embodiments of the system will be provided with hardware, including a processor, and software that is adapted to receive and interpret the received signals and convert this data into visual or audible signals to the surgeon instructing him in which direction and how much to bend the articulation section or to twist the endoscope. Preferably the directions will be quantified, e.g. "you are very close—a fine adjustment to the left is needed" or "back two clicks (of the rotation knob of the articulation section)". In principle the entire alignment process can be totally automated by providing two electric motors controlled by the system processor and software to bend the articulation section in two mutually perpendicular directions.

Optical Alignment System

The alignment method of the invention uses a laser or limited bandwidth radiation source and the endoscope camera that is usually built from a CCD or CMOS sensor. A thin beam is propagated from the surface of the cartridge and, in the fundoplication procedure, penetrates the esophagus wall the fat tissue and the stomach wall until it is received by the camera on the distal tip of the endo scope. The emitted radiation may be from any part of the electromagnetic spectrum, e.g. in the visible or infrared range, on condition that the optics supports the selected spectral range and the camera is sensitive to the emitted radiation. The wavelength is chosen to reduce the scattering of the light by the medium through which it travels to a minimum. As will be described herein below, to aid in distance measurements the light from the radiation source can be focused by a lens (or lens system) that has a focal length that is longer than the needed distance before inserting the screws. Since optical alignment is preferably based on the imaging means that is implemented in the endoscope and used for visualization during execution of the medical procedure. Thus, if the light sources used to provide illumination during the visualization emit radiation in the same wavelength region as the radiation sources that used for alignment, the light sources that are used for camera illumination must be turned off during alignment to prevent interference with the alignment procedure.

Figure 1:
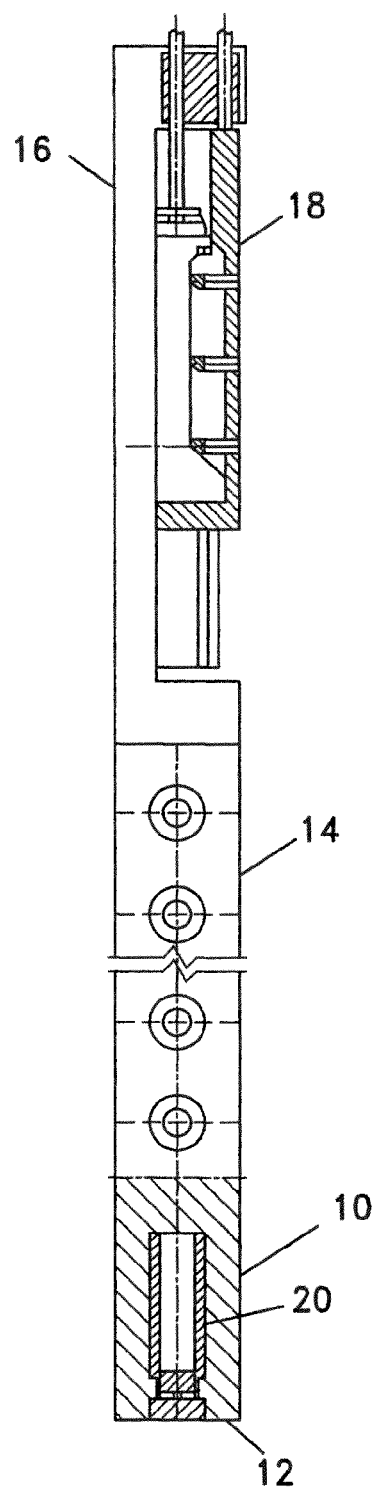
FIG. 1 and FIG. 2 schematically show the distal portion of the insertion shaft of a prior art articulated endoscope with the articulation section in the straight and completely bent configurations respectively.
Figure 2:
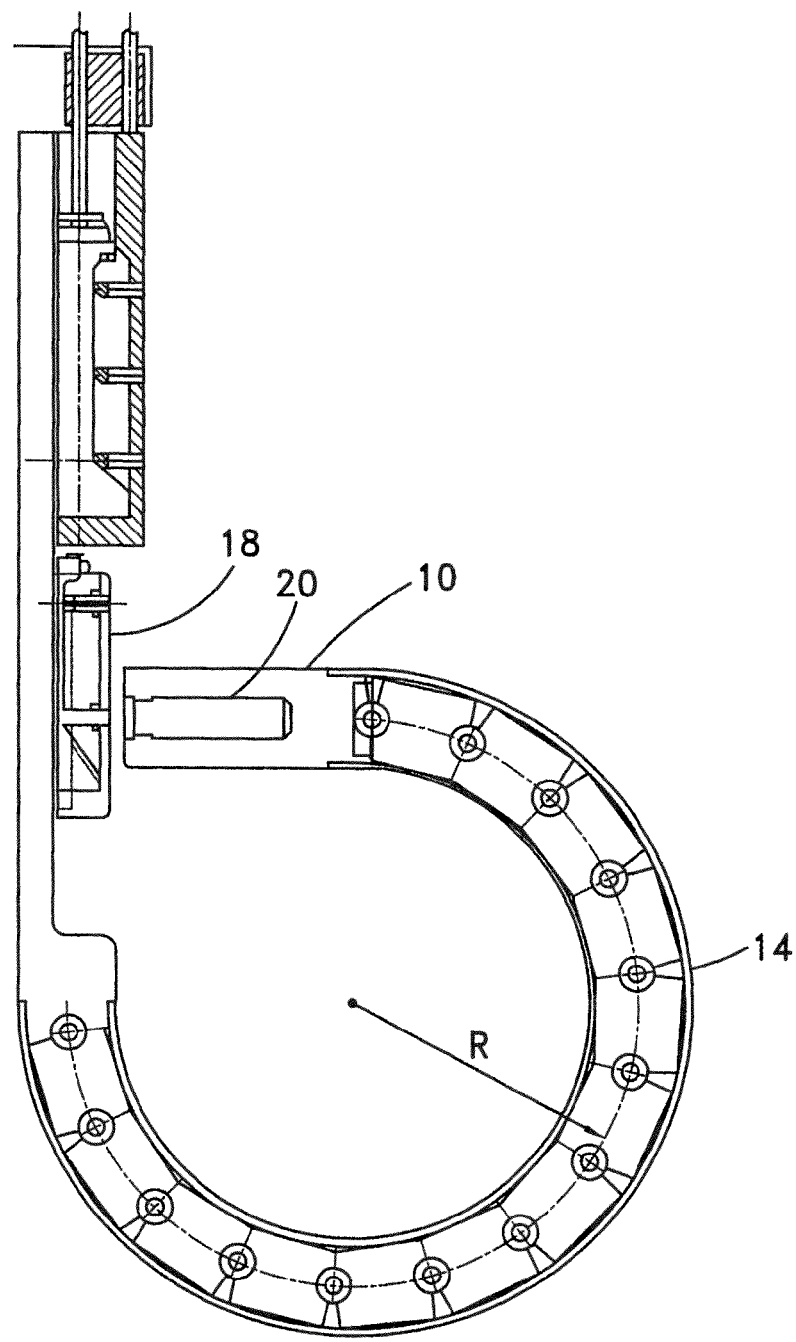
Figure 3:
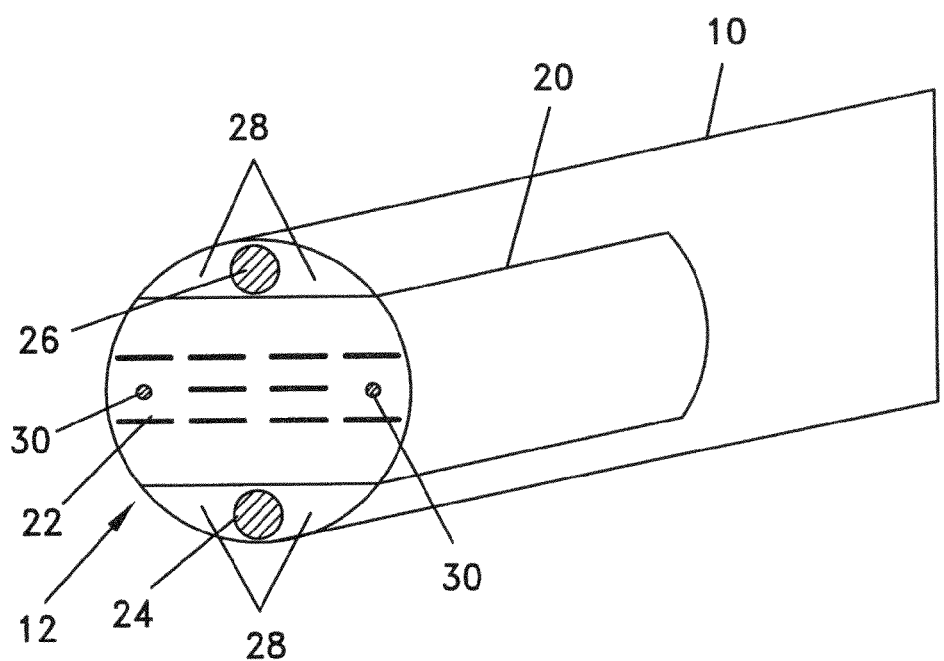
FIG. 3 schematically shows an illustrative distal tip of the endoscope of FIG. 1 with the anvil unit in place.

The basic configuration of the optical alignment system is shown schematically in FIG. 15. A Video camera 48 comprising a high resolution CCD or CMOS imaging element is mounted in imaging channel 26 (see FIG. 3) next to the anvil on the distal face of the distal tip. When the endoscope is bent such that the anvil is brought close to the surface of the cartridge the field of view of camera 48 includes the end of channels 44 that pass through the staple cartridge unit to allow light emitted from laser diodes or LEDs mounted in the hollowed out portion of insertion shaft below the cartridge to exit the face of the cartridge in a direction perpendicular to the surface.

This basic arrangement can be used in several embodiments utilizing either one or two LEDs to provide both qualitative and quantitative information about the relative alignment of the anvil unit and the staple cartridge and the distance between them.

Figure 16:
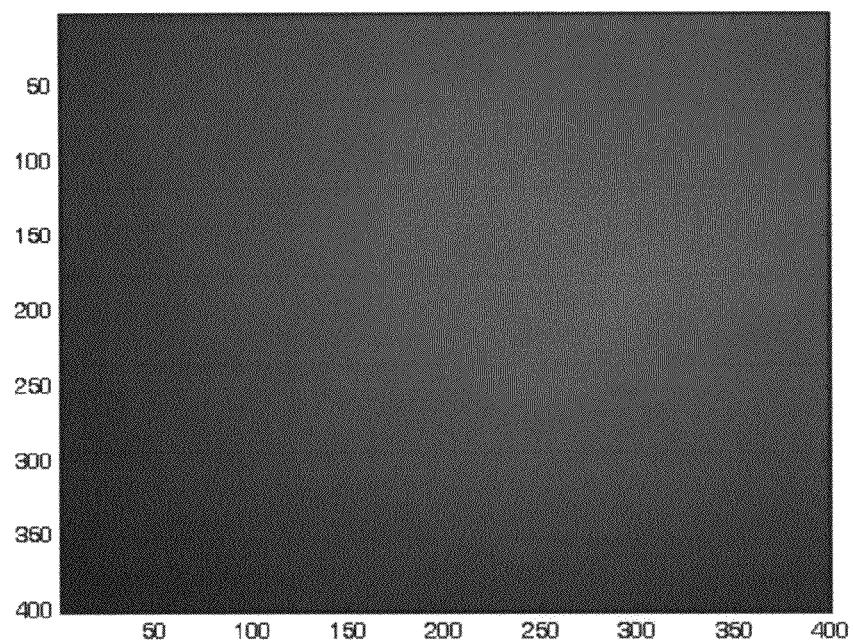
FIG. 16 shows the unprocessed image of the light from a single LED that passes through a layer of swine tissue that is recorded by a CMOS imaging sensor.

Between the face of the anvil unit and the surface of the stapler are one or more layers of tissue that both absorb and scatter the light from the LED that exits from channel 44. The unprocessed image recorded by a CMOS imaging sensor of the light from a single LED that passes through a layer of swine tissue is seen in FIG. 16. The images in FIG. 16 to FIG. 20 are all made using a LED type LXML_PM01__0080 from LUXEON Rebel light source and an OmniVision 6930 CMOS camera (400×400 pixels) imaging device. A filter, which passes only a selected color of the light emitted by the illumination source—green in the current examples—was employed. The filter can be implemented by transferring the green vector from the CMOS. The images are for a 3 mm thick layer of swine tissue. The LED was mounted 2 mm below the tissue without direct connection with the tissue. Using direct connection increases the coupling of the light to the tissue but might harm the tissue because of the heat generated by the light source. This is another reason that the LED is mounted below the stapler cartridge and the light exits the surface of the cartridge through channel 44.

In principle the distribution of the intensity measured by each pixel should give an indication of the relative alignment of image sensor and light source since the intensity should be highest when the sensor and source are exactly opposite one another. However, as is seen from FIG. 16, the scattering by the tissue causes a total smearing of the image from which it is impossible to determine the center of the image. Therefore some sort of image processing method must be used to enhance the image.

Figure 17:
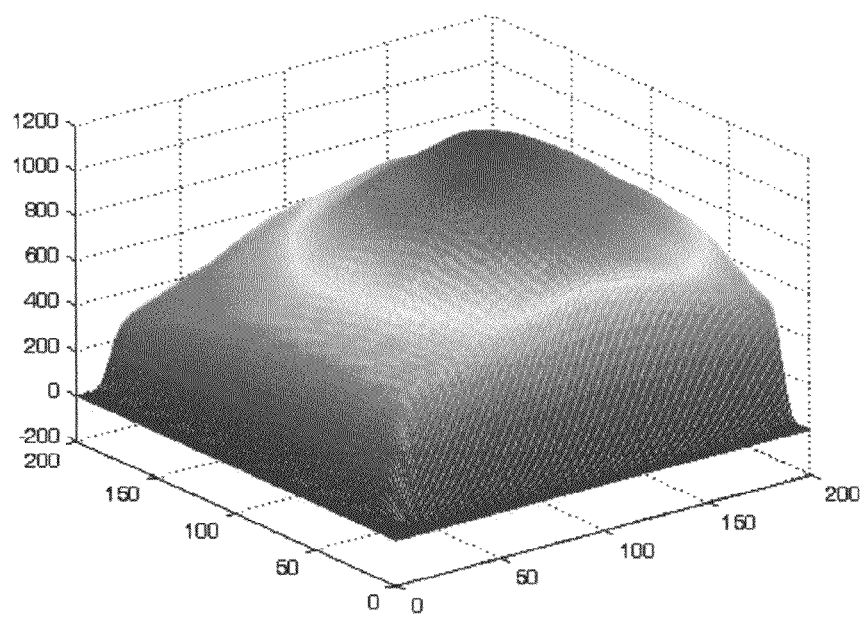
FIG. 17 shows the three dimensional spatial distribution of a portion of the image of the filtered light (green) shown in FIG. 15.
Figure 18:
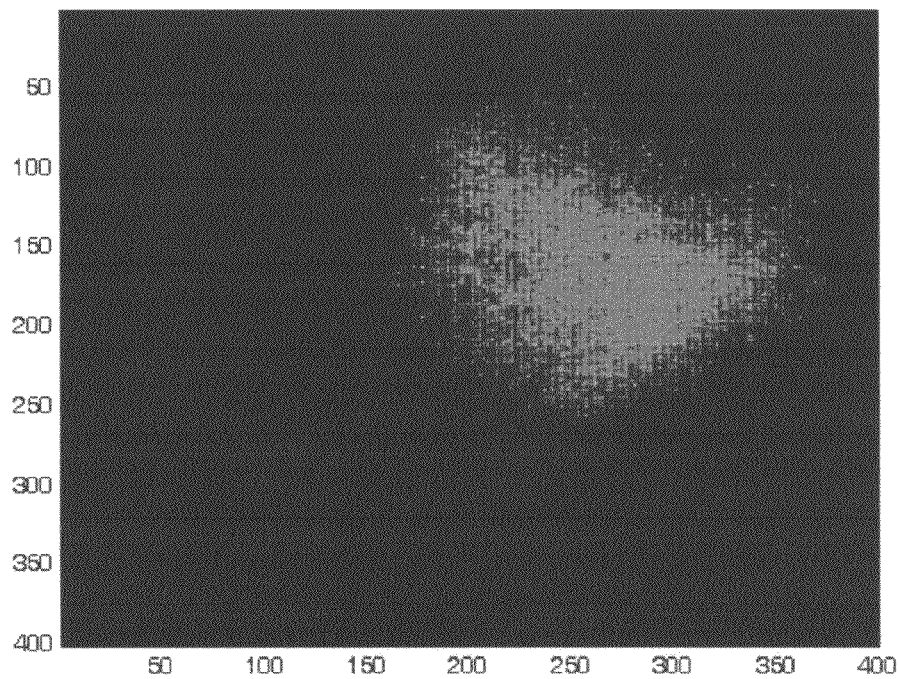
FIG. 18 shows the image of FIG. 15 after applying a normalization procedure.

One enhancement method that can be used for increasing the signal to noise ratio and enables working with relatively low intensity lights sources makes use of the color bandwidth responsivity of the camera at the imaged wavelength. FIG. 17 shows the three dimensional spatial distribution of a portion of the image of the filtered light (green) shown in FIG. 16. In FIG. 17, the "horizontal axes" represent pixel locations and the vertical axis the intensity at each pixel. The signal is then enhanced, for example, by multiplying the intensity at each pixel by a constant that provides a reasonable image on the screen. The constant can be determined arbitrarily by a trial and error search for a value that allows the images to be observed without saturation of the image. A better method of determining the value of the constant is to compare the maximum intensity measured in the unenhanced image to the maximum intensity that the camera is able to measure at the same wavelength. For example, referring to FIG. 17, the maximum intensity is ~700. If the maximum intensity that the camera is able to measure is ~7000, then the multiplication factor to be used in the enhancement will be 10. After multiplying the intensity at each pixel by the multiplication factor, the signal processing phase implements a threshold that cuts the signals below a certain threshold, for example half the peak amplitude or another predetermined value of the intensity or the diameter of an overlaid circle on the screen image (see FIG. 20). An image showing all intensities above the threshold is displayed on a screen by intensity levels or by binary i.e., on or off pixel. The result for the image shown in FIG. 16 after green enhancement, normalization of the signal to peak, and imposing a threshold of half the peak intensity is shown in FIG. 18.

If the apparatus is adjusted such that the center of the screen represents the location at which the system is aligned, the camera is exactly opposite the light source, i.e. the optical axis of camera 48 is aligned with the longitudinal axis of channel 44 (see FIG. 15), then the surgeon adjusts the bending mechanism of the articulation section or twists the endoscope to bring the center of the enhanced image (FIG. 18) to the center of the screen.

Figure 19:
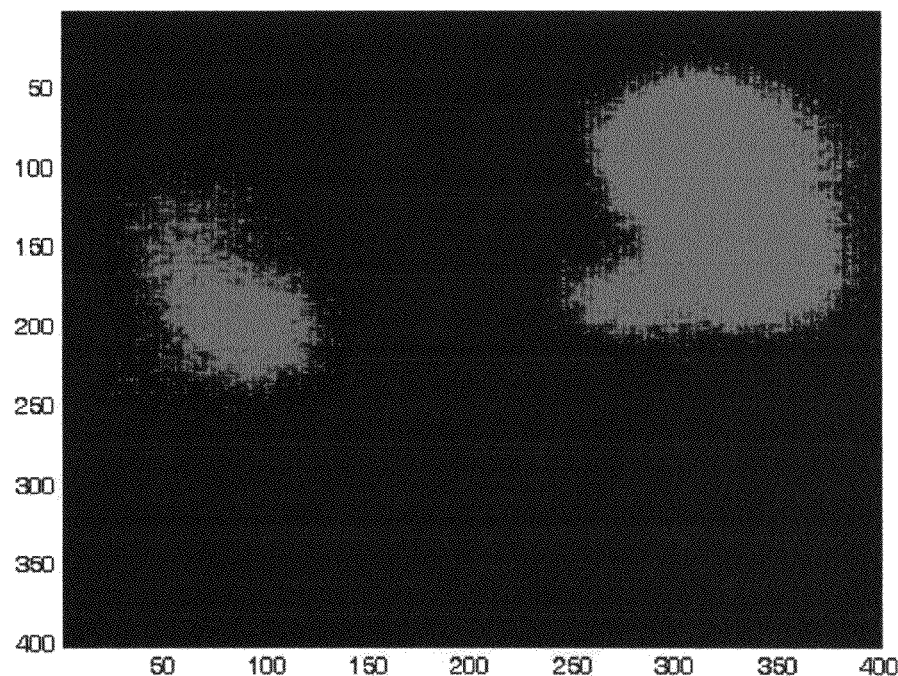
FIG. 19 shows the enhanced camera image of the light from two light sources that has passed through a layer of tissue.

Use of only one light source does not provide a complete solution to the alignment problem. One light source can be used as described above to bring the anvil directly over the cartridge, however there may be a relative twisting between the two components of the stapler such that slots 36 (FIG. 4) through which the legs of the staples exit the cartridge are not parallel to the depressions 22 (FIG. 3) on the face of the anvil. In order to provide a solution to this problem at least two light sources should be used. FIG. 19 shows the camera image of the light from two LEDs that has passed through a layer of tissue after enhancement as described herein above. The components and parameters used to produce FIG. 19 are identical to those used to produce FIGS. 16-18.

Figure 20:
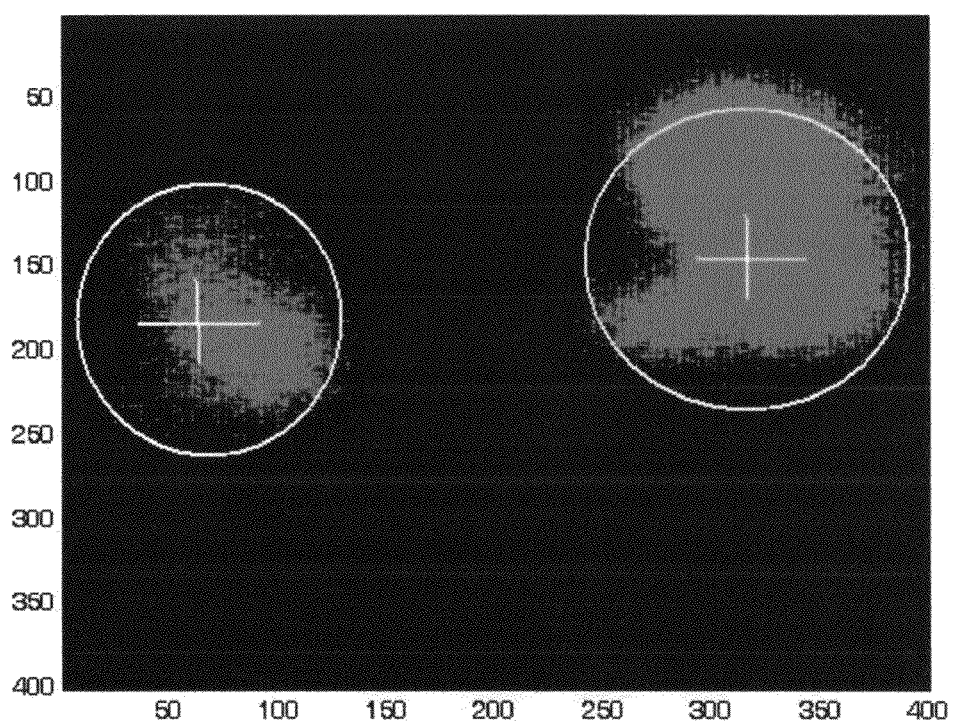
FIG. 20 shows a method of visually achieving simultaneously both the correct alignment and the desired distance between the anvil and cartridge faces.

A method of visually achieving simultaneously both the correct alignment and the desired distance between the anvil and cartridge faces is shown in FIG. 20. FIG. 20 shows the method for the case of two light sources. The same method can be used mutatis mutandis for one or three or more light sources.

As seen in FIG. 20, a screen overlay is drawn comprising two circles having a predetermined diameter and location. The diameters and locations of the centers of the circles are determined such that when the image of the light source is centered on and fills the circle on the screen the anvil tip is in front of the cartridge and the required distance from it. The required distance is typically the distance at which the staples should be fired. If the distance from cartridge and anvil is greater than that desired, then the image on the screen will be smaller than the circle (this is the reason that the focal point is required to be longer that the desired distance). As the camera approaches the light source the centers of the spots on the screen move farther apart and the diameter of the spot increases in size and vice versa; wherein the ratio of the spot diameter to the circle diameter on the overlay is the same as the ratio of the actual to the desired distances. If the cartridge is not locate in front of the anvil then the image will not overlap the drawn circle exactly, nevertheless an elliptical or approximately elliptical image will be seen depending on the angle between the cartridge and anvil. These relationships between the size and location of the enhanced image and the circles on the overlay are used by the surgeon to bring the anvil and cartridge into the correct working relationship. In embodiments of the invention, software is provided as part of a feedback system that automatically determines the corrections that should be made and causes either audible or visual instructions to be given to the surgeon helping to guide him in making the necessary adjustments to the bending section and twisting the endoscope. The exact diameters and locations of the centers of the circles are determined either experimentally or theoretically based on the known dimensions and parameters of the relevant entities, e.g. endoscope, stapler components, camera, and effect of the tissue on light of the selected wavelength that passes through it.

The distance between the illumination aperture, i.e. the top of channel 44 (FIG. 20), and the imaging aperture, i.e. the objective lens of the camera 48, can also be determined directly from the measured intensity as follows:

Let: A=the area of the illumination aperture;
R=the light response of the camera at the wavelength of the light;
z=the distance between the illumination and imaging apertures;
a=the absorption coefficient of the medium between the illumination and imaging apertures at the wavelength of the light;
$I_o$=the intensity of the light at the illumination aperture; and
$I_z$=the intensity of the light at the imaging aperture (distance z).

Two measurements of the light intensity are now made, one a calibration measurement made at known distance $z=z_1$ and the second at unknown distance $z=z_2$.

$$I_{z1} = R*A*I_o*e^{(-az_1)} \qquad \text{equation (1a)}$$

$$I_{z2} = R*A*I_o*e^{(-az_2)} \qquad \text{equation (1b)}$$

Solving one of these equations for $RAI_0$ and substituting in the other results in the following equation for $z_2$:

$$z_2 = I_{z2} \times \frac{e^{(-a_{z1})}}{I_{z1}} = I_{z2}K \qquad \text{equation (2)}$$

Scattering effects have not been taken into account in deriving equation 2. Light scattering by tissues is, relatively, wavelength independent. As discussed herein above in relation to FIG. 16, scattering tends to smear images but its effects can be partially offset by the image processing. Other factors that may reduce the smearing effects of scattering are: (i) the alignment and distance measurements are only required when the illumination and imaging apertures are in close proximity, such that scattered photons will have developed small deviations (ii) tissues are, usually, forward scatterers.

Using equation (2) the distance between anvil and cartridge can be determined directly from the measured intensity without the necessity of applying the image enhancement technique. The video signal from the camera is connected to a processing unit comprising software that comprises instructions to the processor, which when executed solve equation (2) and provides audible or visual information to the surgeon regarding the distance.

The distance between the illumination aperture and the imaging aperture, can also be determined directly from measurements of the light intensity at two different wavelengths as follows:

Let: The two wavelengths be designated by subscripts 1 and 2;

A = the area of the illumination aperture;

$R_1$ and $R_2$ = the light responses of the camera at the two wavelengths;

z = the distance between the illumination and imaging apertures;

$a_1$ and $a_2$ = the absorption coefficients of the medium at the two wavelengths;

$I_{1o}$ and $I_{2o}$ = the intensities of the light of each wavelength at the illumination aperture;

$I_{1z}$ and $I_{2z}$ = the intensities of the light of each wavelength at the imaging aperture (distance z).

The measured light intensities at the two wavelengths at distance z can be expressed as:

$$I_{1z} = R_1 * A * I_{1o} * e^{(-a_1 z)} \quad \text{equation (3a)}$$

$$I_{2z} = R_2 * A * I_{2o} * e^{(-a_2 z)} \quad \text{equation (3b)}$$

From these two equations it follows that:

$$z = \frac{\ln[I_{1z}/I_{2z} * R_2/R_1 * I_{2o}/I_{1o}]}{(a_2 - a_1)} \quad \text{equation (4)}$$

In equation (4) the ratio $I_{2o}/I_{1o}$ is unknown but it can be determined from a simple calibration method, which replicates the actual measurements with the exception that the medium between the illumination and imaging apertures does not absorb the light of either wavelength. If $S_{1z}$ and $S_{2z}$ are the measured intensities for the absorption free medium and $a_1 = a_2 = 0$ is substituted in equations (3a) and (3b), it can be shown that:

$$R_2/R_1 * I_{2o}/I_{1o} = S_{2z}/S_{1z} \quad \text{equation (5)}$$

Equation (5) can be substituted in equation (4), yielding the following equation for z:

$$z = \frac{\ln[I_{1z}/I_{2z} * S_{2z}/S_{1z}]}{(a_2 - a_1)} \quad \text{equation (6)}$$

The use of two wavelengths allows higher resolution measurement of the distance than the single wavelength method. In order to increase the accuracy of the measurements one of the wavelengths is selected in the near infrared where tissue absorption is high and the other wavelength is selected in the low visible range where tissue absorption is low.

Although embodiments of the invention have been described by way of illustration, it will be understood that the invention may be carried out with many variations, modifications, and adaptations, without exceeding the scope of the claims.

The invention claimed is:

1. An elongated medical device, said device comprising an image sensor located at a first location on said device and at least one source of light and a staple cartridge unit of a tissue stapling device located at a second location on said device, wherein said image sensor and said at least one light source cooperate to function as an alignment system when said device is inserted into a patient and configured such that at least one layer of said patient's tissue is positioned between them in order to carry out a medical procedure.

2. The medical device of claim 1, wherein the image sensor is an imaging means that is implemented in the device and used for visualization during execution of the medical procedure.

3. The medical device of claim 2, wherein the imaging means that is implemented in the device is a video camera comprising either a CCD or a CMOS imaging element.

4. The medical device of claim 1, wherein the one or more light sources are mounted on or just below the surface of the staple cartridge unit.

5. The medical device of claim 1, wherein the one or more light sources are mounted at the second location below the staple cartridge unit and the light emitted from one of said one or more light sources passes through one or more channels and exits the face of said staple cartridge unit, if there is more than one channel, as parallel beams of light.

6. The medical device of claim 5, wherein the light sources are replaced by one or more optical fibers or coherent fiber optic bundles that conduct light having one or more wavelengths through the interior of said device from its proximal end to the entrance to each of the one or more channels that pass through the staple cartridge unit.

7. The medical device of claim 1, comprising a filter which passes only selected wavelengths of the light emitted by the light source.

8. The medical device of claim 1, wherein the alignment system is connected to an external system comprising hardware, including a processor, a display screen, and software that is adapted to receive and interpret the received signals from the image sensor and convert these signals into visual or audible signals to the surgeon instructing him how much to configure said device in order to carry out a medical procedure.

9. The medical device of claim 8, wherein the processor comprises software adapted to execute image processing methods to enhance the image recorded by the image sensor to increase the signal to noise ratio and provide a usable image on the display screen.

10. The medical device of claim 9, wherein the distribution of the intensity measured by each pixel in the enhanced image is used to provide an indication of the position of the image sensor relative to the light source.

11. The medical device of claim 9, wherein two or more light sources are used and the distribution of the intensity measured by each pixel in the enhanced image is used to provide an indication of the alignment of the image sensor relative to the light source.

12. The medical device of claim 11, comprising a screen overlay comprising one circle for each light source used, said circle having a predetermined diameter and location, wherein the diameters of said circles and locations of the centers of said circles are determined such that when the image of the each light source is centered on and fills its respective circle on the screen said device is correctly configured in order to carry out the medical procedure.

13. The medical device of claim 12, wherein, when the image of the each light source is not centered on and/or does not fill its respective circle on the screen, the relationships between the size and location of the images on the screen and the circles on the overlay are used by the surgeon to bring the elements of the device into the configuration required to carry out the medical procedure.

14. The medical device of claim 1, comprising an optical alignment system, wherein the distance between the light source and image sensor is determined directly from measurements of the reflected light intensities from two light sources, wherein each of said two light sources has a different wavelength.

* * * * *